United States Patent
Ridgel et al.

(10) Patent No.: US 9,802,081 B2
(45) Date of Patent: Oct. 31, 2017

(54) BIKE SYSTEM FOR USE IN REHABILITATION OF A PATIENT

(71) Applicants: Angela L. Ridgel, Lakewood, OH (US); Hassan Mohammadi-Abdar, Lakewood, OH (US); Fred M. Discenzo, Mayfield Heights, OH (US); Kenneth A. Loparo, Cleveland, OH (US)

(72) Inventors: Angela L. Ridgel, Lakewood, OH (US); Hassan Mohammadi-Abdar, Lakewood, OH (US); Fred M. Discenzo, Mayfield Heights, OH (US); Kenneth A. Loparo, Cleveland, OH (US)

(73) Assignees: KENT STATE UNIVERSITY, Kent, OH (US); CASE WESTERN RESERVE UNIVERSITY, Cleveland, OH (US)

( * ) Notice: Subject to any disclaimer, the term of this patent is extended or adjusted under 35 U.S.C. 154(b) by 25 days.

(21) Appl. No.: 14/966,443

(22) Filed: Dec. 11, 2015

(65) Prior Publication Data
US 2016/0166881 A1 Jun. 16, 2016

Related U.S. Application Data

(60) Provisional application No. 62/091,214, filed on Dec. 12, 2014.

(51) Int. Cl.
*A63B 24/00* (2006.01)
*A61B 5/00* (2006.01)
(Continued)

(52) U.S. Cl.
CPC ........ *A63B 24/0087* (2013.01); *A61B 5/4833* (2013.01); *A61B 5/6895* (2013.01);
(Continued)

(58) Field of Classification Search
CPC . A63B 24/00; A63B 24/0062; A63B 24/0006; A63B 24/0087; A63B 24/0084;
(Continued)

(56) References Cited

U.S. PATENT DOCUMENTS

| 5,890,995 | A  | * | 4/1999 | Bobick  | A63B 24/0084 434/247 |
| 6,902,513 | B1 | * | 6/2005 | McClure | A63B 24/0006 482/4 |

(Continued)

*Primary Examiner* — Glenn Richman
(74) *Attorney, Agent, or Firm* — Renner, Kenner, Greive, Bobak, Taylor & Weber Co., L.P.A.

(57) ABSTRACT

A system for use in rehabilitation of a target patient is provided. The system includes at least two bicycle devices for use by the target patient and a second operator other than the target patient. The at least two bicycle devices each include pedals. At least one of the pedals may have at least one sensor mounted thereon for monitoring operation of the first bicycle device and the target's condition. A servomotor is coupled to the pedals for providing gear-like resistance or pedal assistance for the at least two bicycle devices. A controller is programmed to electrically couple the at least two bicycle devices to each other.

16 Claims, 9 Drawing Sheets

(51) Int. Cl.
*A63B 21/28* (2006.01)
*B62K 3/14* (2006.01)
*G06F 19/00* (2011.01)
*A63B 22/06* (2006.01)
*A63B 21/005* (2006.01)
*A63B 22/00* (2006.01)
*A63B 22/02* (2006.01)

(52) U.S. Cl.
CPC ............... *A63B 21/28* (2013.01); *B62K 3/14* (2013.01); *G06F 19/3443* (2013.01); *G06F 19/3481* (2013.01); *A63B 21/0058* (2013.01); *A63B 22/0048* (2013.01); *A63B 22/02* (2013.01); *A63B 22/0605* (2013.01); *A63B 22/0664* (2013.01); *A63B 2022/0094* (2013.01); *A63B 2024/0093* (2013.01); *A63B 2225/20* (2013.01); *A63B 2225/50* (2013.01)

(58) Field of Classification Search
CPC . A63B 22/0605; A63B 22/0048; A63B 22/02; A63B 22/0664; A63B 2225/20; A63B 2225/50; A63B 21/0058; A63B 21/28; A63B 5/4833; A63B 2022/0094; A63B 2024/0093
USPC ......................................................... 482/1–9
See application file for complete search history.

(56) References Cited

U.S. PATENT DOCUMENTS

| | | | |
|---|---|---|---|
| 8,784,270 B2* | 7/2014 | Ashby | A63B 21/005 482/1 |
| 2010/0035726 A1* | 2/2010 | Fisher | A63B 24/0084 482/8 |
| 2013/0274069 A1* | 10/2013 | Watterson | A63B 24/0087 482/9 |
| 2014/0171267 A1* | 6/2014 | Alberts | A61H 1/02 482/6 |

* cited by examiner

BIKE SYSTEM FOR USE IN REHABILITATION OF A PATIENT

CROSS-REFERENCE TO RELATED APPLICATIONS

This application claims priority to U.S. Provisional Patent Application Ser. No. 62/091,214, filed Dec. 12, 2014, by the same title.

BACKGROUND OF THE INVENTION

This disclosure relates to a method and apparatus for rehabilitation of a patient with movement or neurological disorders attendant to strokes. Parkinson's disease, Huntington's disease, Alzheimer's disease and the like. The invention finds particular application in using a bike system with a controller to sense, control and dynamically alter a rehabilitation program for a patient with Parkinson's disease. While the invention herein will be described with particular reference to Parkinson's disease, it will be readily appreciated that it is relevant to treatment of those conditions just mentioned.

Parkinson's disease (PD), which affects approximately one million people in the U.S. and 7 to 10 million people worldwide, is a chronic, progressive neurological disorder that is characterized by the loss of dopaminergic neurons in the brainstem. The main symptoms of the disease are movement disorders, and include shaking or tremor, muscle stillness and rigidity, and slowness of physical movements (i.e., bradykinesia). As PD progresses, the combined motor and non-motor symptoms often lead to reduced independence and increased reliance on caregivers and the healthcare system. The economic impact of PD, including treatment, social security payments, and lost income from inability to work, is estimated up to $25 billion per year in the United Suites.

There is no known cure for this degenerative disease that results in progressive deterioration of motor skills along with other reduced physical and mental functions. The accepted treatment for PD is medication (e.g. levodopa) and in some cases surgical intervention (e.g. deep brain stimulation). These treatments only mask the symptoms and do not slow progression of the disease. Furthermore, they often have undesirable side effects, are costly and can introduce additional health risks. Considering these deficiencies, there is it need for innovative treatments to prevent, delay disease progression, and improve the symptoms of PD.

Recent studies have shown that exercise and movement therapies have significant benefits for individuals with PD, but there is little consensus on the optimal mode or intensity. Several studies have documented the benefits of high-cadence tandem cycling for motor function improvement in PD riders. However, the effective factors of exercise (e.g., rpm, intensity, intervention type, duration of the exercise, and the like), which constitute an optimal exercise intervention for PD patients, are still unknown. For example, each PD patient has different symptoms and skill levels, which makes it challenging to design a general rehabilitation system that gives the maximum benefit to all PD patients. Moreover, progression of the disease often requires re-assessments and modifications of the motor rehabilitation programs.

Several studies have shown a significant improvement in patient motor skills from tandem cycling. However, even with the exceptional results reported from tandem cycling, large-scale use of the tandem cycling paradigm for exercise therapy is not feasible for several reasons. First, tandem cycling requires an able-bodied trainer to assist in pedaling that is not reasonable in large-scale clinical deployment or in-home use. Second, variability in trainer pedaling speed, stamina, and response to the PD rider's performance creates variations that make data analysis and conclusions in clinical studies difficult to generalize. Third, there are a number of factors, such as cadence, foot position and workload that can affect the biomechanics of cycling and resultant performance. Many motorized single-rider stationary exercise bikes are commercially available today that can provide a pre-programmed load profile for the rider. However, it has not been possible to reproduce the dynamics of the tandem bike cycling paradigm using currently available motorized cycles.

SUMMARY OF THE INVENTION

In one embodiment, a system for use in rehabilitation of one or more target patients is provided. The system includes at least two bicycle devices for use by the target patient(s) and a second operator other than the target patient. The at least two bicycle devices each include pedals. At least one of the pedals may have at least one sensor mounted thereon for monitoring operation of the first bicycle device and the target's condition. Alternatively, the monitoring can be undertaken by other means, such as the drive for a servomotor coupled to the pedals for providing gear-like resistance or pedal assistance for the al least two bicycle devices. A controller is programmed to electrically couple the at least two bicycle devices to each other and control the servomotor.

In another embodiment, a system for use in therapy of a target patient is provided. The system includes at least one bicycle device for use by the target patient and a second operator other than the target patient. The bicycle devices include pedals. At least one of the pedals may have at least one sensor mounted thereon for monitoring operation of the first bicycle device and the target's condition. A servomotor is coupled to the pedals for providing gear-like resistance/assistance for the at least one bicycle device. A controller is programmed to acquire data related to target patient performance obtained from the at least one sensor, and adjust operation of the system responsive to the target patient performance.

In a further embodiment, a system for use in rehabilitation of a target patient is provided. The system includes a first bicycle device for the target patient. The first bicycle device includes pedals. At least one sensor monitors operation of the first bicycle device and the target's condition. A servomotor is coupled to the pedals for providing gear-like resistance/assistance for the first bicycle device. A second bicycle device is provided for a second operator other than the target pattern. The second bicycle device includes pedals.

At least one sensor monitors operation of the second bicycle device and the second operator's condition. A servomotor is coupled to the pedals for providing gear-like resistance for the second bicycle device. A controller is electrically programmed to couple the first and second bicycle devices to each other, acquire data related to target patient performance obtained from the at least one sensor, and adjust operation of the system responsive to the target patient performance.

Further scope of the applicability of the presently described embodiments will become apparent from the detailed description provided below. It should be understood, however, that the detailed description and specific examples, while indicating particular embodiments of the present disclosure, are given by way of illustration only, since various changes and modifications within the spirit and scope of the present disclosure will become apparent to those skilled in the art.

BRIEF DESCRIPTION OF THE DRAWINGS

The presently described embodiments are described in the construction, arrangement, and combination of the various parts of the device, and the method, whereby the objects contemplated are attained as hereinafter more fully set forth, specifically pointed out in the claims, and illustrated in the accompanying drawings in which:

DETAILED DESCRIPTION OF ILLUSTRATIVE EMBODIMENTS

Figure 1:
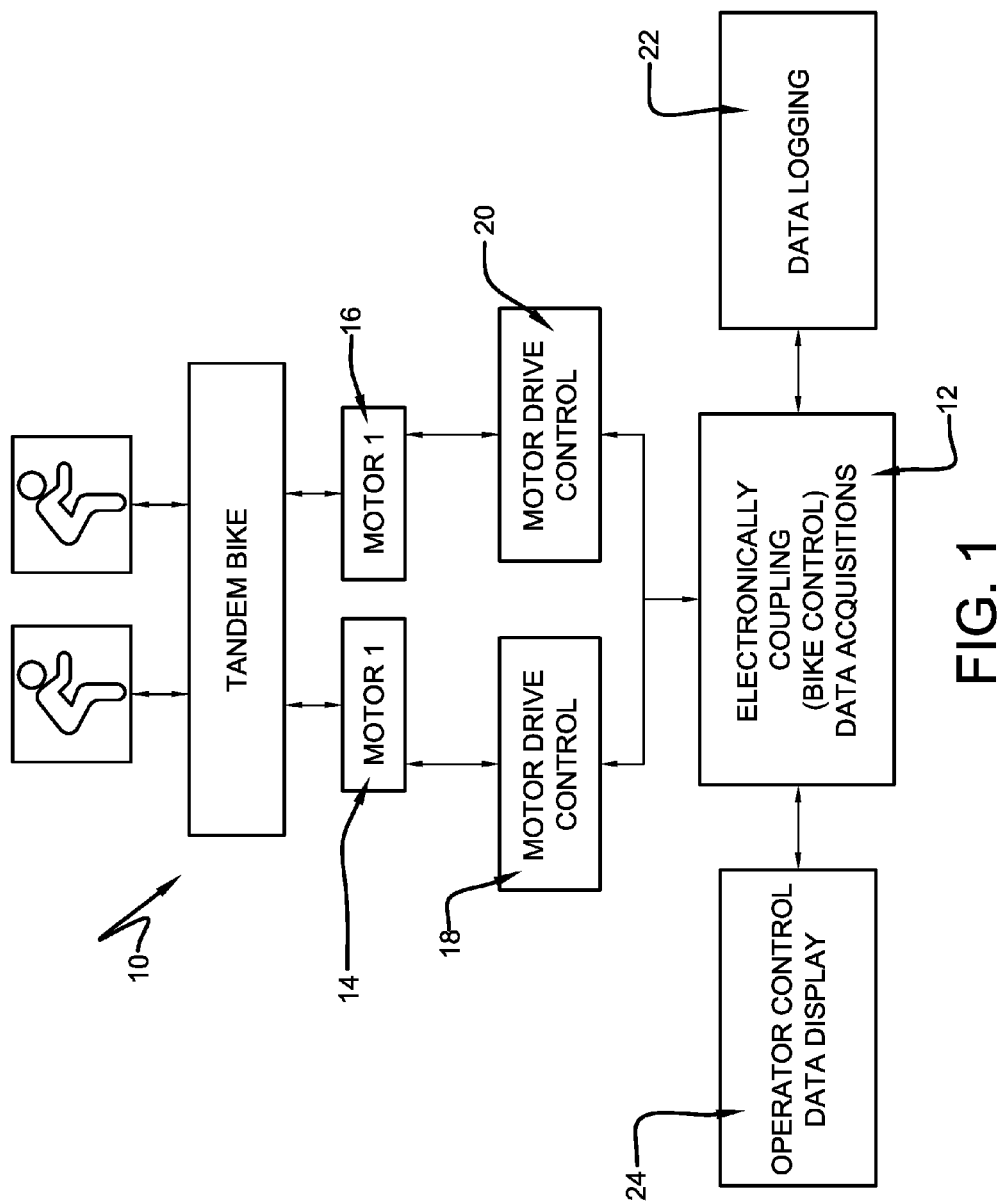
FIG. 1 is a first schematic view of a tandem bike according to one embodiment of the present disclosure.

As shown in FIG. 1, a tandem bike or system 10 which accommodates the interaction and power sharing between a trainer (i.e., a leader) and a rider (i.e., a follower) is provided. Advantageously, the tandem bike 10 eliminates the need for a mechanical coupling of pedals (not shown in FIG. 1) of the tandem bike 10 by replacing the mechanical coupling with electronic coupling. In one example the electronic coupling is provided by a programmable logic controller 12.

The tandem bike 10 operates in two modes: 1) data acquisition; and 2) real-time bike control. Advantageously, a common chain that mechanically connects the two riders is removed, and the controller 12 electrically links two or more users together. For example, the controller 12 in operating mode 1 is used to collect real-time performance data from the users (e.g., a trainer and a rider) using sensors and devices connected to, for example, bike pedals, as described in more detail below. The synchronized data samples are analyzed to determine the coupling characteristics (such as amplification, attenuation, drag, elasticity, and backlash, and the like) in the electrical coupling. Subsequent data analyses examine the response of the trainer to disturbances (from the rider) and develop a model of how the trainer interacts with the rider. For example, the controller 12 is programmed to collect performance data from each of the target patient and the second operator. In the context of the invention, the controller 12 may be any appropriate programmable logic controller, dedicated microprocessor, computer or similar device.

In operating mode 2, the model and information obtained during operating mode 1 are used to connect the trainer and rider electronically in the tandem bike 10. In this case, the trainer and the rider are electronically linked as if they were mechanically connected through a standard tandem bicycle drivetrain (i.e. chain-coupled sprockets). For example, the controller 12 generates a mathematical model of an interaction between the target patient and the second operator from the performance data. The mathematical model provides the electrical coupling of the two riders.

In another example, the controller 12 is programmed to collect data from other similar patients that are stored in a database. In such instances, the controller 12 includes a data-mining processor (not shown) that collects data related to patients with similar conditions and symptoms as a target patient. The data-mining processor is programmed with a classification algorithm to mine a historical database (not shown) to collect the data related to patients with similar conditions and symptoms as a target patient. From this collected data, the controller 12 is programmed to generate a statistical model. The controller 12 is then programmed to adjust operation of the tandem bike 10 responsive to each of the mathematical model and the statistical model.

From the mathematical model and/or the statistical model, the controller 12 is programmed to dynamically alter the cadence and torque experienced by the trainer and rider. In one example, the controller 12 alters the cadence and torque experienced by the trainer and rider through a real-time power management control algorithm, as described in more detail below. In another example, the controller 12 alters the cadence and torque experienced by the trainer and rider through a machine-learning algorithm. In this mode, the tandem bike 10 operates with a trainer and rider in both acquisition and closed-loop control modes, or with a single rider (i.e., no trainer) where inputs to the rider are provided by an input reference trajectory inputted by a trainer into the controller 12.

In some instances, a trainer model (not shown in FIG. 1) is integrated with the controller 12 of a single tandem bike 10. The trainer model serves to provide the feel and experience of a tandem bike to a rider on a single automated bike. The testing, data analysis, and model attenuation may be performed to validate the test platform for use in subsequent clinical trials and to enable improved motor function benefits for PD riders.

Figure 2:
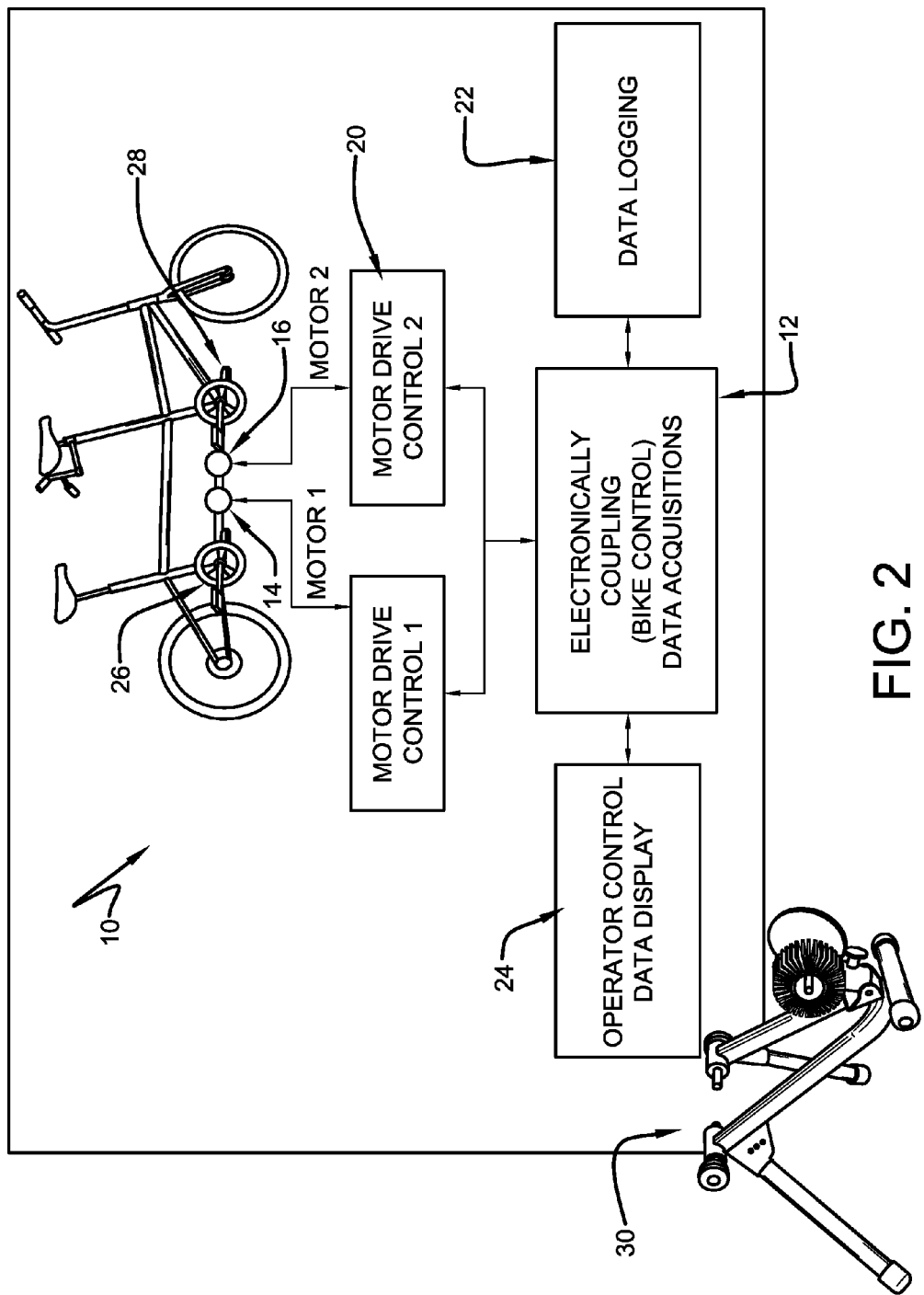
FIG. 2 is a second schematic view of the tandem bike of FIG. 1.

As shown in FIG. 2, the tandem bike 10 includes a plurality of servomotors 14 and 16 that each includes a motor drive control 18 and 20 associated therewith. Various sensors (not shown in FIG. 2) are also coupled to a portion of the tandem bike 10 (e.g., the pedals). The controller 12, the servomotors 14 and 16, the motor drive controls 18 and 20, and the sensors are each coupled to a data acquisition system 22. The testing, data analysis, and model development, along with other outputs from use of the tandem bike 10 are displayed on a display 24 operably connected to the controller 12. Unlike typical tandem bikes, the bike 10 has non mechanical interconnection between the tandem sections as by a chain or belt, but rather a virtual interconnection through the controller 12, motor drive controls 18, 20 and associated motors.

The servomotors 14 and 16 are capable of providing gear-like resistance to a user. Since the tandem bike 10 imitates two-person tandem bike behavior, each of the two servomotors 14 and 16 service a separate rider. Each of the servomotors 14 and 16 is wired to an associated one of the motor drive controls 18 and 20, which are wired to the controller 12, thereby forcing the motors 14 and 16 to react to the users' increase or decrease in pace.

The tandem bike 10 may be commercially available and modifiable, or, alternatively, may be specifically designed and constructed. In one example, the tandem bike 10 can be rack mounted to enable stationary cycling. In another example, the tandem bike 10 can be movable by pedaling, in which case the tandem bike carries a battery power source, PLC and the like. In some instances, the tandem bike 10 is modified by removing the mechanical coupling (i.e., the shared chain). In some examples. The servomotors 14 and 16 are directly connected to crank assemblies (not shown in FIG. 2) through auxiliary sprockets and chains, as well as replacing the bikes' cranksets with the power-meter crankset. The tandem bike 10 requires the servomotors 14 and 16 to provide resistance by attachment to bike pedals 26 and 28 with two additional chains (not shown). In one example, the power management control algorithm of the controller 12 alters the speed and torque delivered to the pedals 26 and 28 by the servomotors 14 and 16.

Figure 3:
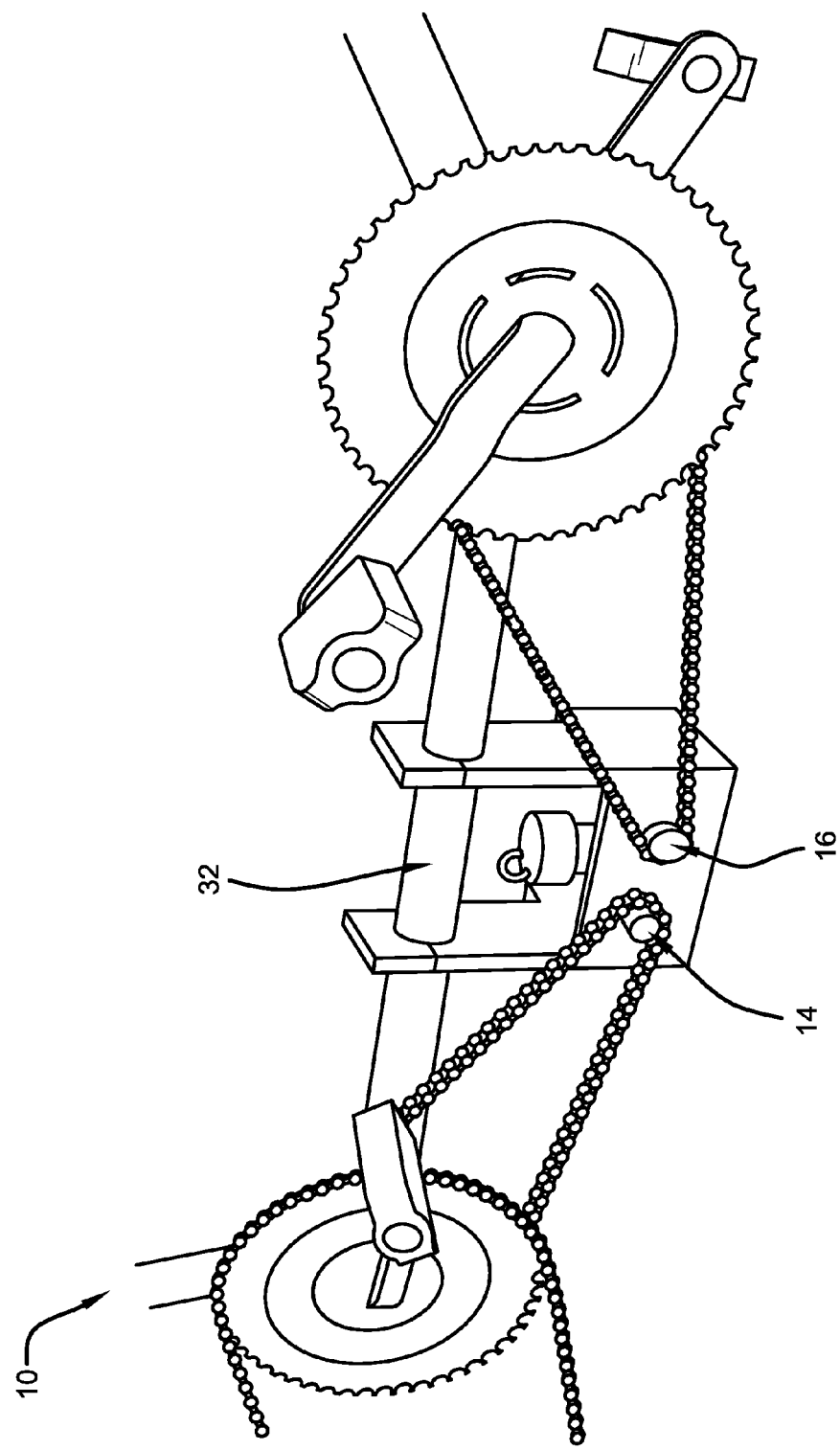
FIG. 3 is a plan view showing the coupling of the tandem bike of FIG. 1.

In one example, a commercially available tandem bike 10 is outfitted with the controller 12, the servomotors 14 and 16, the motor drive controls 18 and 20, and the data acquisition system 22. To establish the electrical control, for operating modes 1 and 2, the chain (not shown) is removed, and the controller 12, the servomotors 14 and 16, and the motor drive controls 18 and 20 link the riders electronically. A rack 30 is provided for rack-mounting the bike to provide stationary operation thereof. As shown in FIG. 3, the servomotors 14 and 16 are installed on a chassis 32 of the tandem bike 10.

Figure 4:
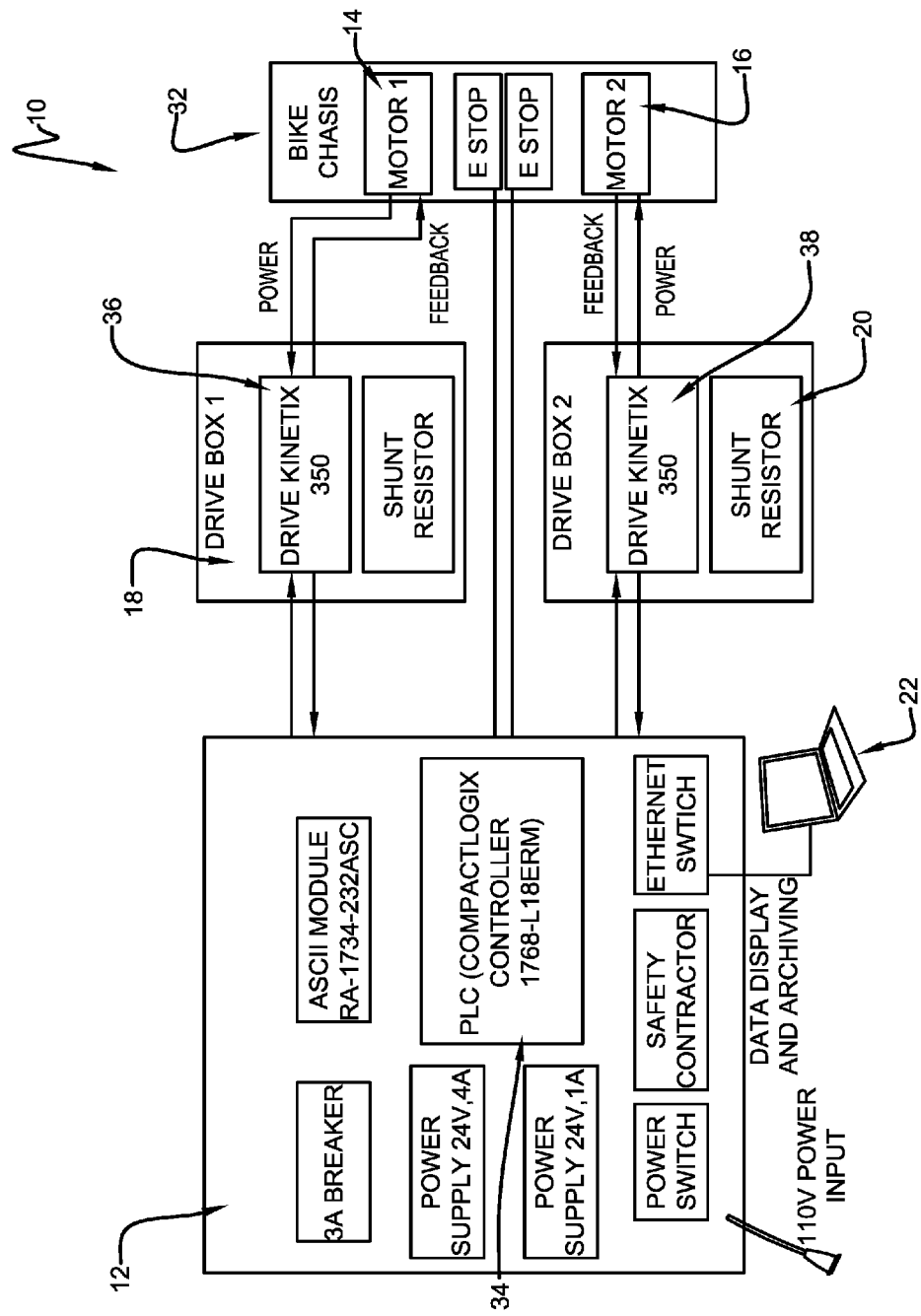
FIG. 4 is a schematic view of a controller of the tandem bike of FIG. 1.
Figure 5:
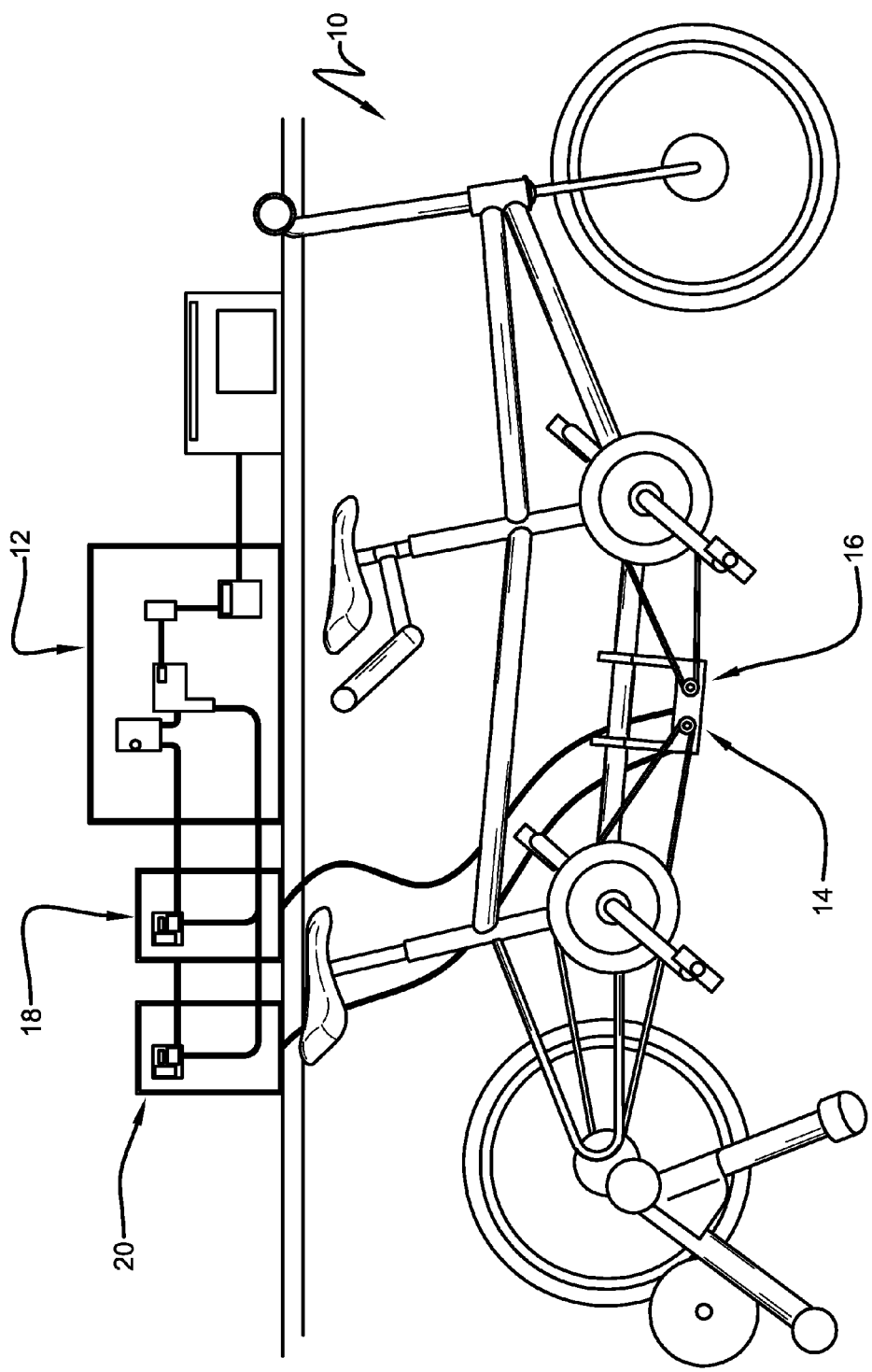
FIG. 5 is a plan view of the assembled tandem bike of FIG. 1.
Figure 6:
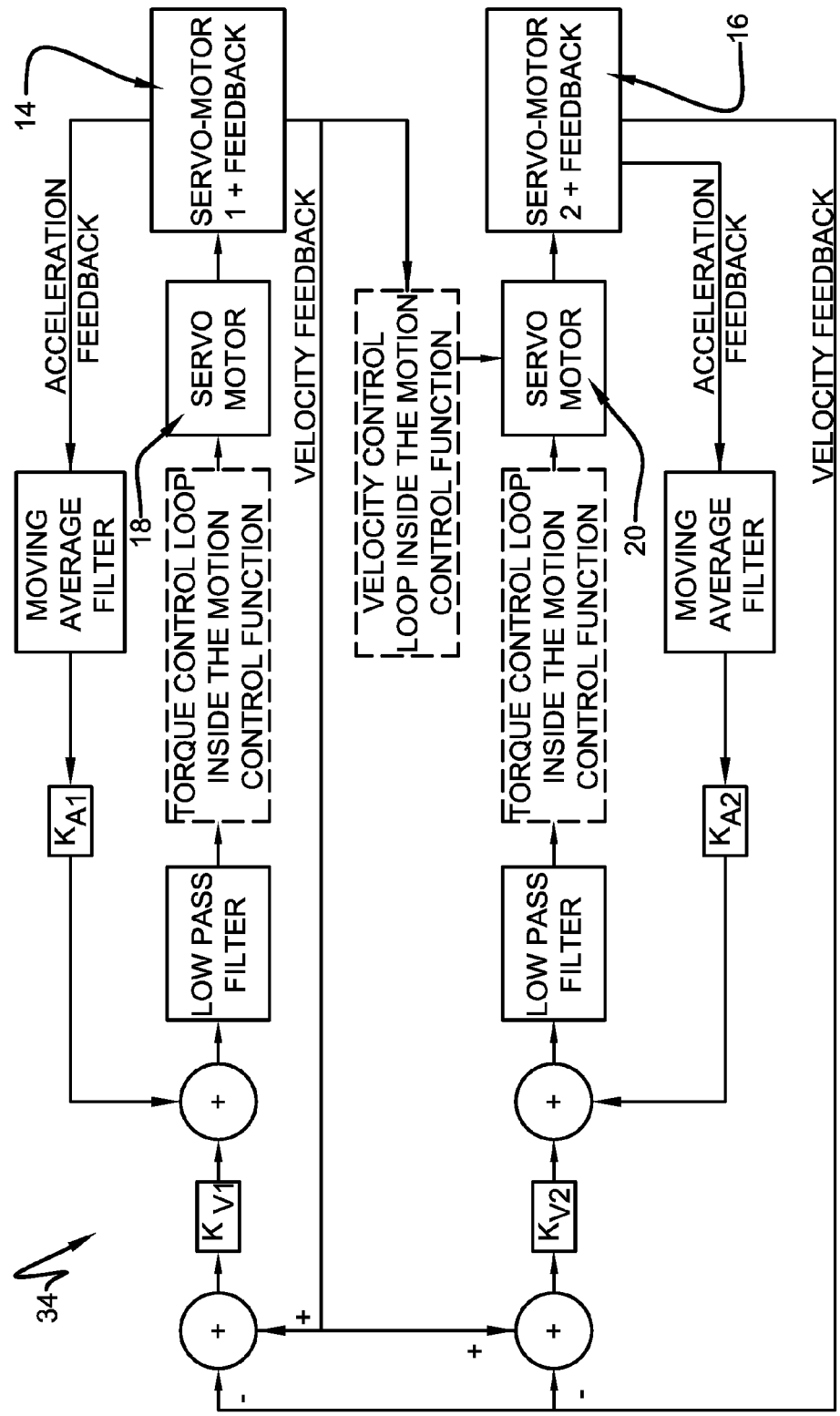
FIG. 6 shows a control architecture for the bike controller of FIG. 4.

As shown in FIG. 4, the controller 12 is operably connected to the tandem bike 10. The controller 12 includes a logic processor 34. The logic processor 34 communicates with the display 22 and the motor drive controls 18 and 20 through an Ethernet network to send and receive commands and data. The logic processor 34 determines the appropriate motor speed and load (e.g., torque) values and transmits this information to the motor drive controls 18 and 20. Each motor drive control 18 and 20 includes a high-speed inner loop controller 36 and 38 that are operably connected to the controller 12 and the first and second servomotors 14 and 16, respectively. The loop controllers 36 and 38 provide the appropriate voltage and current to the servomotors 14 and 16 to continually maintain the operating state of the servomotors 14 and 16 specified by the logic processor 34. As shown in FIGS. 5 and 6, motor feedback from the servomotors 14 and 16 to the motor drive controls 18 and 20 is used to maintain proper motor speed and torque in spite of load disturbances introduced by the rider. For example, as shown in FIG. 6, the data can pass through a feedback data loop which includes a series of filters (e.g., low pass filters, moving average fillers, and the like).

As shown in FIG. 4, the tandem bike 10 is also equipped with the display 22 (e.g., a rugged touch screen device). The display 22 serves as the human-machine interface for the tandem bike 10 and communicates with the logic processor 34 through Ethernet to send the parameters entered by the trainer to the logic processor 34 and to receive and display the required data from the logic processor 34. The display 22 also provides a graphical plot showing historical values for bike and rider operation.

The controller 12 includes multiple software programs and control algorithms developed to run and control the tandem bike 10. The control algorithms that operate the tandem bike 10 are developed and implemented into the logic processor 34. The developed algorithms are downloaded to the logic processor 34 to provide real-time control of operation of the tandem bike 10. The logic processor 34 includes the control algorithms for use with the development and operating platform (i.e. the display 22, the servomotors 14 and 16, the motor drive controls 18 and 20) provided with the tandem bike 10. Multiple commercially-available software development tools are used to develop the algorithms and routines, establish communication with the devices to download the code, and to transmit and display the data. In one example, the logic processor 34 includes a main control algorithm that electrically couples the cranksets of the tandem bike 10 to each other. In another example, the logic processor 34 includes algorithms for programming and controlling the servomotors 14 and 16, thereby allowing the servomotors 14 and 16 to be controlled and run independently. Software in the logic processor 34 is developed such that the rider tracks the speed of the trainer, while the two users share the power required to pedal the tandem bike 10.

Figure 7:
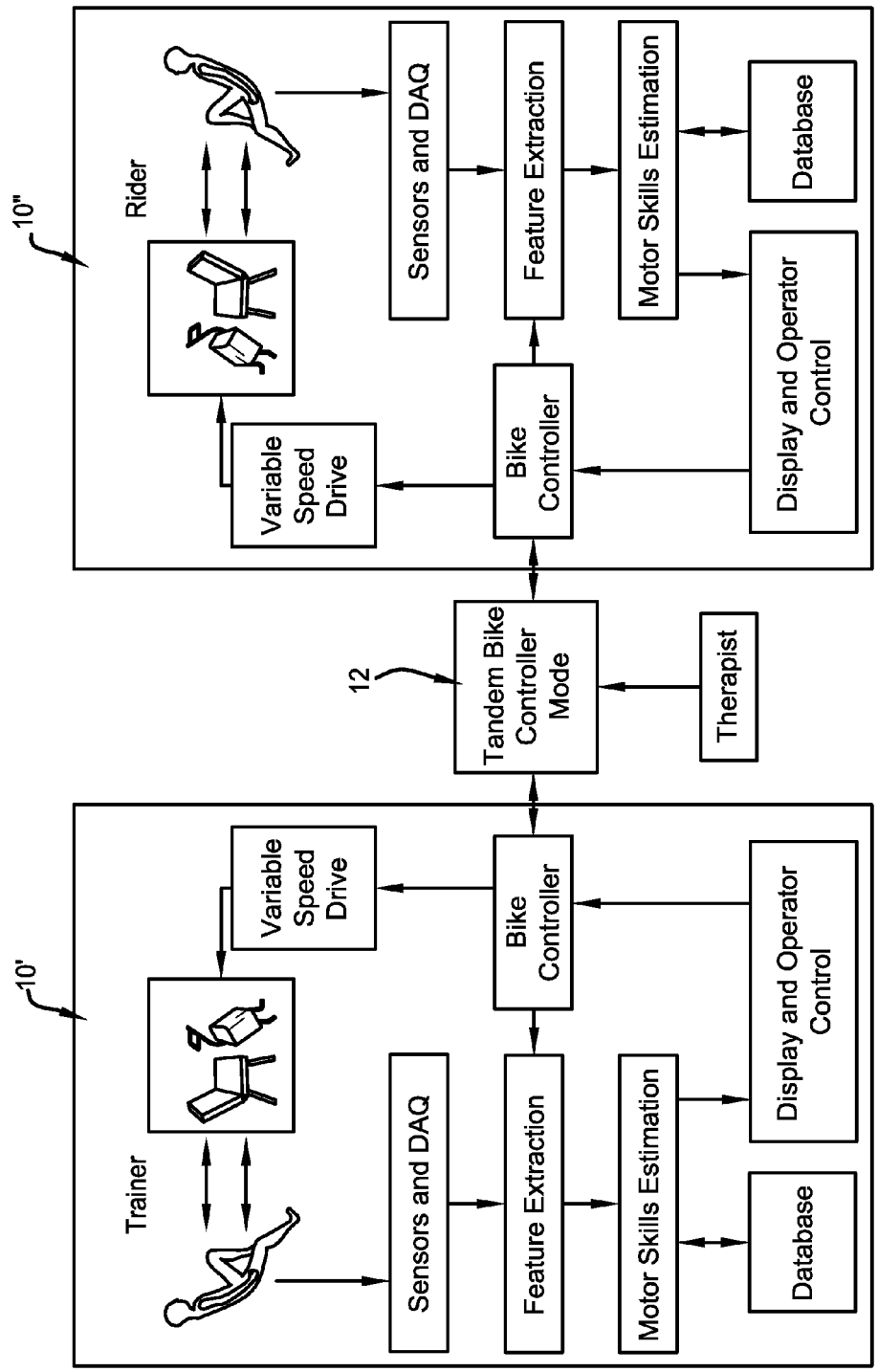
FIG. 7 is a schematic view of an electrical coupling of two bike systems according to another embodiment or the present disclosure.

The logic processor 34 electronically couples the servomotors 14 and 16 in such a way that the tandem bike 10 emulates a mechanical coupling thereof. In other words, in contrast to a standard tandem bike with a mechanical coupling between the two sets of pedals, the invention employs an electronic coupling that emulates the mechanical coupling. A preferred situation occurs when the riders have exactly the same cadence (i.e., velocity) and power is shared between the riders. In one example, as shown in FIG. 7, the logic processor 12 electronically links two riders on the tandem bike 10 by coupling two single-rider bikes 10' and 10" to behave like the tandem bike 10 shown in FIG. 1, thereby allowing users to bike together in different locations and feel like they are cycling on the tandem bike 10 linked with a traditional chain coupling. The desired signals can be transferred via internet or other data networks, both wired and wireless. The two single-rider bikes 10' and 10" replicate the behavior of one of the tandem riders, advantageously allowing single PD riders to benefit from the effects of tandem cycling, even within their own homes. For example, when the operator of the first bike 10' takes the larger portion of the power/torque, the operator of the second bike 10" provides the lower amount of power, and vice versa. In one example, a target patient operates one of the single-rider bikes 10' and a second user different from the first user a trainer, another patient, and the like) operates the other of the single-rider bikes 10". In another example, the target patient operates one of the single-rider bikes 10' and controller 12 operates the other of the single-rider bikes 10". The concept of the invention applies not only to bikes and the like, but other therapeutic devices as well, such as stepping machines, ellipticals, treadmills and the like.

In some embodiments, the controller 12 is programmed to include a human in the loop control system (not shown) programmed to monitor the operation of the tandem bike 10. In such examples, the loop control system is programmed to perform at least one of the following tasks: react and adapt to changes initiated by at least one of the target patient and the second operator; detect and accommodate inappropriate interaction by at least one of use target patient and the second operator; accommodate different skill level and competency levels between the target patient and the second operator; detect and respond to wear and fault conditions of the system; and protect the at least one of the target patient and the second operator and the system. The loop control system operates as a "fail-safe" for the tandem bike 10 by operating as a protection mechanism. In some instances, the human in the loop control system can include a plant component and a plant model component. For example, the plant exponent includes actual output data of the target patient, the second operator (e.g., the trainer, the other patient, the controller 12, and the like) and the tandem bike 10. Stated another way, the plant component encompasses the tandem bike 10 and the users. In another example, the plant model component includes an expected output data of the target patient, the second operator, and the system. The human in the loop control system is programmed to adjust the operation of the tandem bike 10 based on a comparative analysis of the differences between the actual output data of the plant component and the expected output data of the plant model component. This residual analysis may serve to identify equipment problems, rider condition (e.g., fatigue) or model deficiencies.

Figure 8:
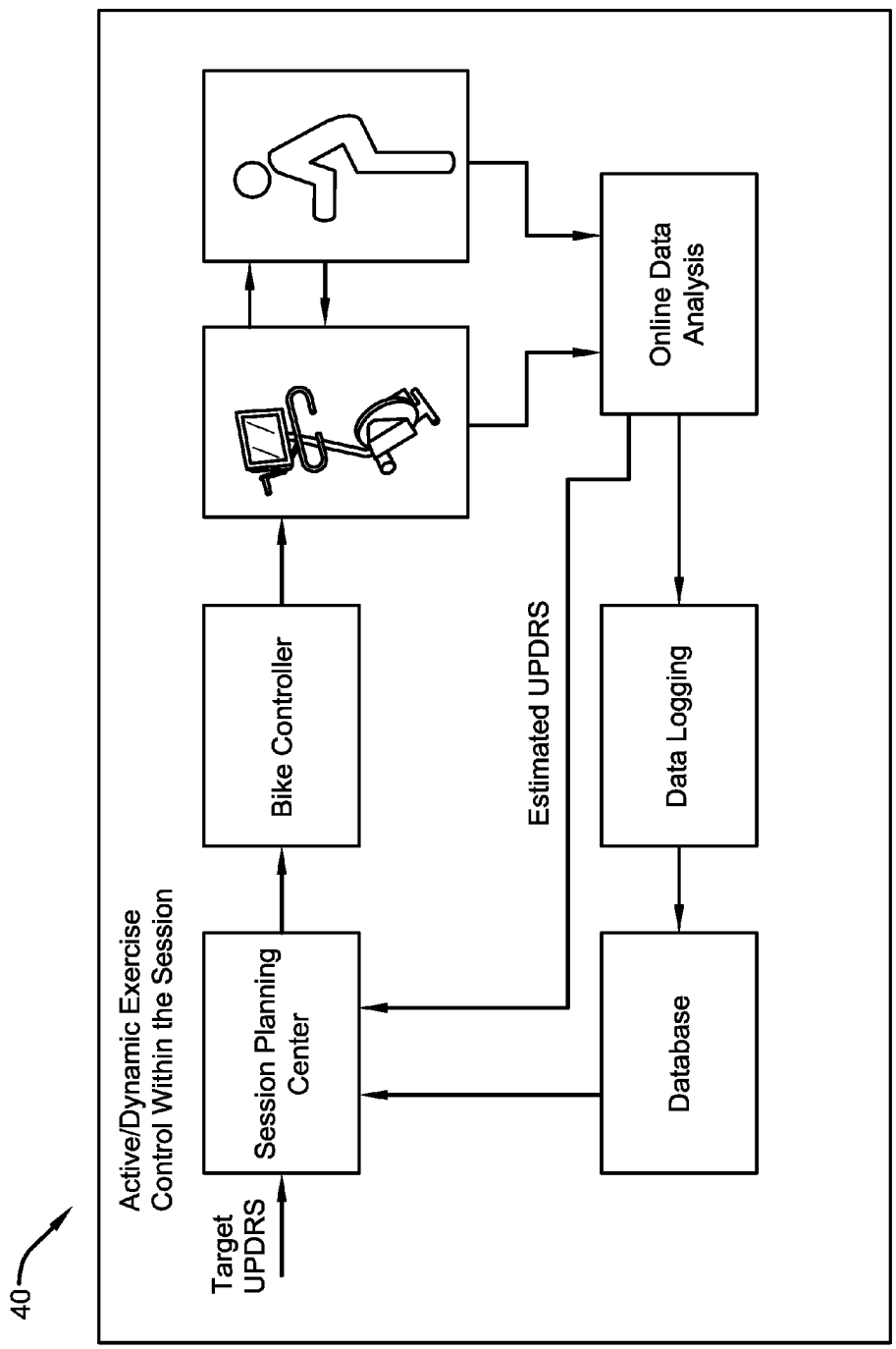
FIG. 8 presents an algorithm of a controller of the bike systems of FIG. 7; and, FIG. 9 is a second schematic view of the algorithm of a controller of the bike systems of FIG. 7.

In another embodiment designated by the numeral 40 as shown in FIG. 8, real-time data signals as well as previously recorded data (e.g., changes in motor function, bike signals, physiological data, and the like) are used to compute adaptive exercise parameters within the exercise session as well as session by session. The adaptive exercise system 40 exports appropriate control parameters for the tandem bike 10 considering target Unified Parkinson's disease rating scale (UPDRS) changes. During the exercise, bike and patient signals are being processed in real-time to evaluate the exercise quality and calculate the expected UPDRS change. The adaptive exercise system 40 applies the results to the controller 12 to modify the control parameters. These data are also logged to be used in future sessions. Accordingly, the system optimizes the rehabilitation paradigm during a therapy session us well as between sessions, using target and projected UPDRS (Unified Parkinson's Disease Rating Scale) on a therapy device. Moreover, the controller 12 provides a platform for automatically controlling rider-bike interaction to optimize the benefit from accelerated dynamic cycling. Although the foregoing is discussed in regards to UPDRS, other PD measures and standards may be used to estimate rider condition or rider motor skill level.

The exercise system 40 is dynamic and adaptive, providing the optimal exercise program for the rehabilitation of individuals with different skill levels and improvement profiles. Exercise programs are optimized for each patient based on the individual conditions and skill level to provide the most benefit for the patient. Moreover, online data analysis permits rapid identification of problems, rider fatigue, or unusual behavior and allows for corrective control action and provides superior rider safety. Furthermore, data logging and remote access capability could be used by physicians, trainers, and therapists interested in monitoring in-home progress of PD patient exercise. Some or all elements of session planning, data analysis, data logging, or database may be done on multiple processors, remote processors, or cloud-based platforms. For example, the components of the tandem bike 10 may be packaged in a single module, or distributed geographically and linked by the multiple processors, the remote processors, and/or the cloud-based platforms.

In one example, as shown in FIG. 8, the adaptive exercise system 40 is a closed loop adaptive control of the exercise parameters of the tandem bike 10 during a training session. During a planning session, appropriate control parameters of the tandem bike 10 are adjusted in view of target UPDRS changes. For example, during a training session, signals from the users and the tandem bike 10 are processed in real-time by the controller 12 to evaluate the exercise quality and calculate the expected UPDRS change to create a feedback loop. In another example, the controller 12 may input disturbances in order to enhance therapeutic value or to probe the tandem bike 10 for improved state estimation. The feedback loop applies the results to the current planning session to modify control parameters of the tandem bike 10. This data can also be stored and used in future planning sessions. The controller 12 also provides a platform for automatically controlling user-tandem bike 10 interaction to optimize accelerated dynamic cycling benefits. A control output may include tandem bike 10 values and/or user control values or parameter limits or constraints (e.g., limits on rider input torque, heart rate, and the like). For example, the control parameters can include speed, torque, load share amount, pedal coupling lag, disturbance amplification, and the like.

Figure 9:
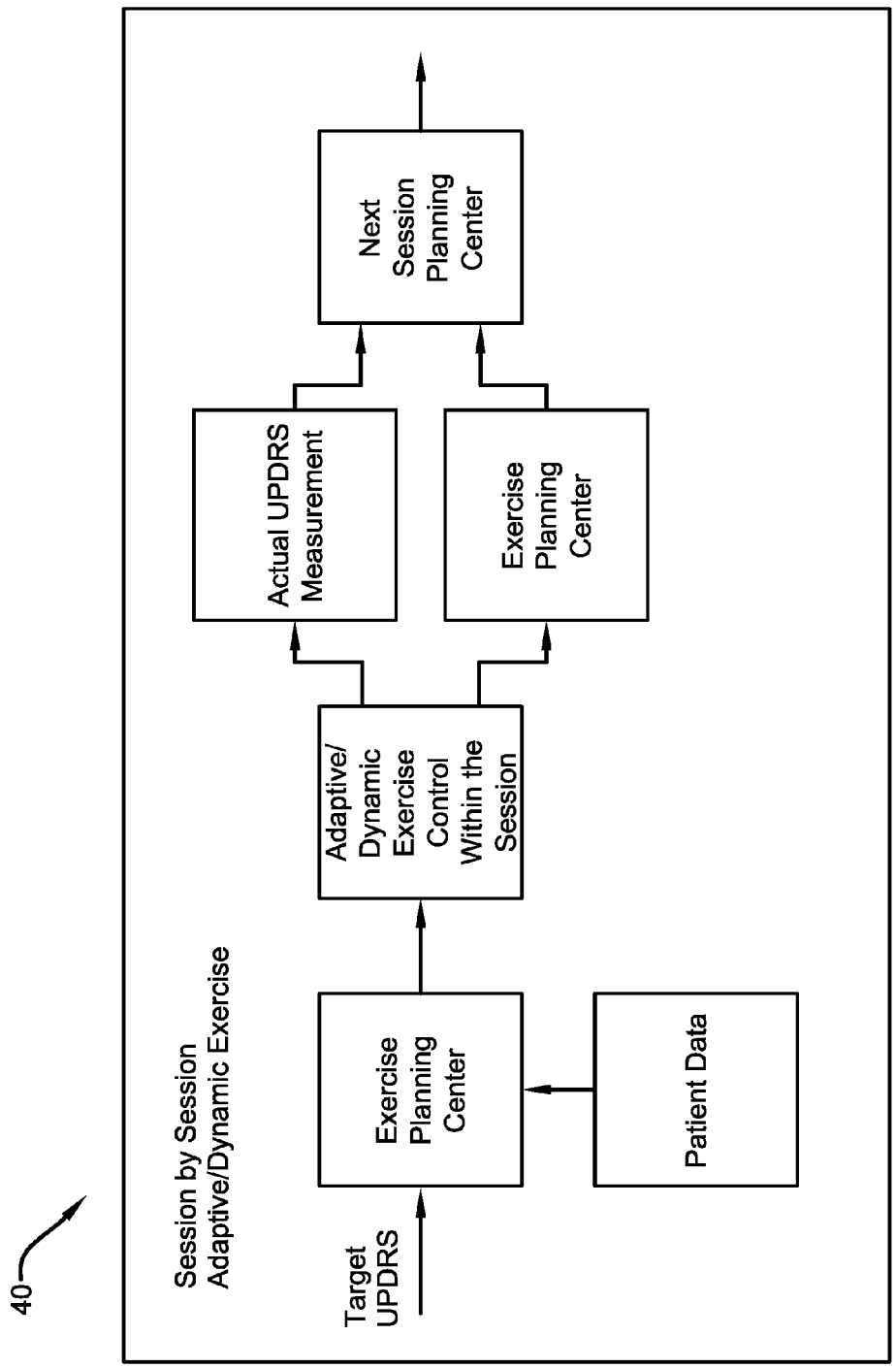

In another example, as shown in FIG. 9, the adaptive exercise system 40 also includes a session by session control scheme, which extends the adaptive exercise system 40 to future exercise sessions. An exercise planning module provides appropriate data and instructions related to user/tandem bike 10 performance to the adaptive exercise system 40 during a training session based on previous user/tandem bike 10 data and target UPDRS data. The controller 12 runs and controls the tandem bike 10 during the rehabilitation session based on the information provided by the planning module. Alter each rehabilitation session, actual UPDRS data is measured, and expected UPDRS data is calculated, based on recorded data from the user and the tandem bike 10 during the rehabilitation session. The actual UPDRS data and the expected UPDRS data is collected and stored for use by the planning module for planning the next rehabilitation session, although the planning module may be implemented without an actual UPDRS measurement. From this, individuals with different skill levels and improvement profiles can be optimized for use with the tandem bike 10 and the controller 12. In one example, the optimization process may prescribe specific set point value for some variables. In another example, the optimization process may also specify constraints or permissible ranges for some variables (e.g., speed, heart rate, and the like). In addition, the adaptive exercise system 40 also permits rapid identification of problems, rider fatigue, or unusual behavior for corrective control action and provides safely for the user(s), as described in more detail below.

To do so, in some instances, the adaptive exercise system 40 can include a plant component and a plant model component. For example, the plant component includes actual output data of the target patient, the second operator (e.g., the trainer, the other patient, the controller 12, and the like) and the tandem bike 10. In another example, the plant model component includes an expected output data of the target patient, the second operator, and the system. The human in the loop control system is programmed to adjust the operation of the tandem bike 10 based on a comparative analysis of the differences between the actual output data of the plant component and the expected output data of the plant model component.

In other instances, the adaptive exercise system 40 can include a model-based control model for providing the user with an experience similar to riding a tandem bicycle and a captain model (i.e., an expert model) for sensing capabilities of the rider and adjusting a process control for the tandem bike 10 accordingly. In one example, the controller 12 is programmed to emulate an experience of riding a tandem bike for the user via the control model. In another example, the captain model can be a domain expert model and/or an expert operator model. For example, the captain model can sense capabilities of the users and adjust the operation of the tandem bike 10 accordingly. Specifically, the captain model is programmed to assess parameters related to the rider (e.g., health condition, skill level, and the like) and alter a display, prompts, and/or limits on a rider input device (not shown). In addition, during a rehabilitation session, the captain model is programmed to sense a user's capabilities through the session and set an optimum therapy regimen and work load to maximize the benefit for the user while protecting the user from injury and/or fatigue.

In further instances, the controller 12 is programmed to decouple the tandem bike 10 from the user in the controller for segmenting and concentrating expertise and control information focused on a particular aspect of the control of the tandem bike 10. As a result, the segmenting and concentrating expertise can detect faults or anomalous conditions, effectively prescribe an appropriate response to observed changes in the tandem bike 10 or the user. Consequently, the controller 12 can more effectively analyze the operation of the tandem bike 10, the controller 12, and the user(s). To do so, the controller 12 can include a therapist model processor for input by a trainer; a physician model processor for input by a trainer; a prediction model processor for predicting performance output data of the target patient; an optimization model processor for optimizing one or more parameters of a training program; and/or a machinery maintenance model for monitoring to changes to the at least one bicycle device.

In light of the foregoing, it will be appreciated that the concept of the invention can be provided in multiple control architectures, providing both local and remote system operation and coordination. A single controller may both control and acquire data from multiple sites operating either concurrently or in different time frames, acquiring data from the sensors of remote devices and adapting the operation of those devices as a function of the user's needs and capabilities. The electronic nature of the system, replicating physical and mechanical structures, provides a unique opportunity to alter the coupling between pedal cranks such as either attenuating or amplifying disturbances, replicating various characteristics or anomalies and regulating the timing of various operations. The data processing and storage operations are substantially unlimited when the system is configured for a cloud-based operation, including both cloud databases and cloud-based analytics. The number of sites and users that can be accommodated with such a cloud-based operation is substantially limitless. When the users are geographically distributed, pedal synchronization can be electronically achieved as if the geographically separated riders were on the same virtual bike. Timing sequences for accommodating network delays for both pedal control and pedal synchronization are also readily available through the centralized digital control. The data processing and electronic controls of the invention also provide for enhanced safety and security, providing a means of actually confirming rider identity by noting and comparing the riding characteristics of various users, and by employing diagnostics and prognostics attendant to various sensors connected to the rider, the bike, the motor drive, and the like. Additionally, and as presented herein, the system accommodates the establishment of a database, including historical data on intervention and resulting outcomes of the various riders utilizing the system, and accommodates data assessment for use, modification, and adaptation.

Thus it can be seen that the various aspects of the invention have been satisfied by the structures and techniques presented herein. The above description merely provides a disclosure of particular embodiments of the present disclosure and is not intended for the purposes of limiting the same thereto. As such, the present disclosure is not limited to only the above-described embodiments. Rather, it is recognized that one skilled in the art could conceive alternative embodiments that fall within the scope of the present disclosure. For example, while the above description describes specific processors, algorithms, and routines, it will be appreciated that any type of hardware or software can be used with the present disclosure.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A system for use in rehabilitation of a target patient, the system comprising:
at least two bicycle devices for use by the target patient and a second operator other than the target patient, the at least two bicycle devices each including:
pedals, indicating operation of the first bicycle device and the target's condition;
a servomotor coupled to the pedals for providing resistance or assistance for the at least one bicycle device; and
a controller programmed to electrically couple the at least two bicycle devices to each other, said controller including a human in the loop control system programmed to:
react and adapt to changes initiated by at least one of the target patient and the second operator;
detect and accommodate inappropriate interaction by at least one of the target patient and the second operator;
accommodate different skill level and competency levels between the target patient and the second operator;
detect and respond to wear and fault conditions of the system; and/or
protect the at least one of the target patient and the second operator and the system.

2. The system of claim 1, wherein the controller is further programmed to acquire performance data related to each of the at least two bicycle devices.

3. The system of claim 1, wherein the controller is further programmed to:
collect performance data from each of the target patient and the second operator; and
generate a mathematical model of an interaction between the target patient and the second operator from the performance data.

4. The system of claim 3, wherein the mathematical model provides the electrical coupling between the at least two bicycle devices.

5. The system of claim 3, wherein the controller is further programmed to:
generate a statistical model developed from patient data of other patients; and
adjust operation of the system responsive the mathematical model and the statistical model.

6. The system of claim 5, wherein the controller adjusts operation of the system by being further programmed to:
dynamically alter a cadence and a torque experienced by each of the target patient and the second operator through a real-time rehabilitation management control algorithm.

7. The system of claim 6, wherein the controller is further programmed to dynamically alter a cadence and a torque experienced by each of the target patient and the second operator through a machine-learning algorithm.

8. The system of claim 1, wherein the system operates with the target patient operating one of the at least two bicycle devices and a second user different from the target patient operating another of the at least two bicycle devices.

9. The system of claim 1, wherein the system operates with the target patient operating one of the at least two bicycle devices and the controller operating another of the at least two bicycle devices.

10. The system of claim 1, wherein the human in the loop control system includes:
a plant component that includes actual output data of the target patient, the second operator and the system; and
a plant model component that includes an expected output data of the target patient, the second operator, and the system.

11. The system of claim 3, wherein the controller is further programmed to:
generate a predictive model developed from patient data of other patients; and
adjust operation of the system responsive to the mathematical model and the predictive model.

12. A system for use in rehabilitation of a target patient, the system comprising:
a first bicycle device for the target patient, said first bicycle device
including:
pedals, at least one of the pedals having at least one sensor mounted thereon for monitoring operation of said first bicycle device and a condition of the target patient;
a servomotor coupled to the pedals for providing resistance or assistance for said first bicycle device;
a controller programmed to:
acquire data related to target patient performance obtained from the at least one sensor; and
adjust operation of the system responsive to the target patient performance;
collect performance data from the target patient; and
generate a mathematical model of an interaction between the target patient and said first bicycle device from the performance data, said mathematical model providing an electrical coupling between said first bicycle device and a second bicycle device, and wherein the target patient operates said first bicycle device and said controller operates said second bicycle device.

13. The system of claim 12, wherein the controller is further programmed to acquire performance data related to each of said first and second bicycle devices.

14. The system of claim 12, wherein the controller includes:

a control model for providing the user with an experience similar to riding a tandem bicycle; and
a captain model for sensing capabilities of the rider and adjust the process control for the system accordingly.

15. A system for use in rehabilitation of a target patient, the system comprising:
a bicycle device for the target patient, said bicycle device including:
pedals, at least one of the pedals having at least one sensor mounted thereon for monitoring operation of said bicycle device and a condition of the target patient;
a servomotor coupled to the pedals for providing resistance or assistance for said bicycle device;
a controller programmed to:
acquire data related to target patient performance obtained from the at least one sensor; and
adjust operation of the system responsive to the target patient; and
wherein the controller includes a human in a loop control system, the human in the loop control system including:
a plant component that includes actual output data of the target patient and the at least one bicycle device; and
a plant model component that includes expected output data of the target patient and the at least one bicycle device.

16. A system for use in rehabilitation of a target patient, the system comprising:
at least one bicycle device for the target patient, the at least one bicycle device including:
pedals, at least one of the pedals having at least one sensor mounted thereon for monitoring operation of the at least one bicycle device and a condition of the target patient;
a servomotor coupled to the pedals for providing resistance or assistance for the at least one bicycle device; and
a controller programmed to:
acquire data related to target patient performance obtained from the at least one sensor; and
adjust operation of the system responsive to the target patient performance,
wherein the controller includes at least one of:
a therapist model processor for input by a trainer;
a physician model processor for input by a trainer;
a prediction model processor for predicting performance output data of the target patient;
an optimization model processor for optimizing one or more parameters of a training program; and
a machinery maintenance model for monitoring to changes to the at least one bicycle device.

* * * * *

UNITED STATES PATENT AND TRADEMARK OFFICE
CERTIFICATE OF CORRECTION

| | |
|---|---|
| PATENT NO. | : 9,802,081 B2 |
| APPLICATION NO. | : 14/966443 |
| DATED | : October 31, 2017 |
| INVENTOR(S) | : Angela L. Ridgel et al. |

It is certified that error appears in the above-identified patent and that said Letters Patent is hereby corrected as shown below:

In the Specification

At Column 1, immediately above "BACKGROUND OF THE INVENTION," add:
-- STATEMENT REGARDING FEDERALLY SPONSORED RESEARCH OR DEVELOPMENT
This invention was made with government support under grant/contract NIH R21HD068846 awarded by National Institutes of Health. The government has certain rights regarding the invention. --

Signed and Sealed this
Thirteenth Day of February, 2024

Katherine Kelly Vidal
*Director of the United States Patent and Trademark Office*